US010688087B2

(12) United States Patent
Karlsson et al.

(10) Patent No.: US 10,688,087 B2
(45) Date of Patent: Jun. 23, 2020

(54) PHARMACEUTICAL COMPOSITIONS AND THERAPEUTIC METHODS EMPLOYING A COMBINATION OF A MANGANESE COMPLEX COMPOUND AND A NON-MANGANESE COMPLEX FORM OF THE COMPOUND

(75) Inventors: Jan-Olof Karlsson, Trondheim (NO); Rolf Andersson, Vikingstad (SE)

(73) Assignee: PLEDPHARMA AB, Stockholm (SE)

( * ) Notice: Subject to any disclaimer, the term of this patent is extended or adjusted under 35 U.S.C. 154(b) by 186 days.

(21) Appl. No.: 13/379,468

(22) PCT Filed: Jul. 6, 2010

(86) PCT No.: PCT/IB2010/053097
§ 371 (c)(1),
(2), (4) Date: Dec. 20, 2011

(87) PCT Pub. No.: WO2011/004325
PCT Pub. Date: Jan. 13, 2011

(65) Prior Publication Data
US 2012/0101066 A1    Apr. 26, 2012

Related U.S. Application Data

(60) Provisional application No. 61/306,348, filed on Feb. 19, 2010, provisional application No. 61/223,204, filed on Jul. 6, 2009.

(51) Int. Cl.
*A61K 31/444* (2006.01)
*A61K 31/506* (2006.01)
(Continued)

(52) U.S. Cl.
CPC .......... *A61K 31/444* (2013.01); *A61K 31/506* (2013.01); *A61K 33/32* (2013.01); *A61K 45/06* (2013.01)

(58) Field of Classification Search
CPC .... A61K 31/444; A61K 31/506; A61K 33/32; A61K 45/06
(Continued)

(56) References Cited

U.S. PATENT DOCUMENTS 6,147,094 A * 11/2000 Towart et al. ................ 514/332
6,258,828 B1    7/2001 Towart et al.
(Continued)

FOREIGN PATENT DOCUMENTS

EP    0936915 B1    10/2002
EP    0910360 B1    11/2002
(Continued)

OTHER PUBLICATIONS

Elst et al ("Spectroscopic and Metabolic Effects of MnCl2 and MnDPDP on the Isolated and Perfused Rat Heart." Investigative Radiology, 1997; 32(10):581-588).*
(Continued)

*Primary Examiner* — Marcos L Sznaidman
*Assistant Examiner* — Rayna Rodriguez
(74) *Attorney, Agent, or Firm* — Porter Wright Morris & Arthur LLP

(57) ABSTRACT

A pharmaceutical composition for treatment of a pathological condition in a patient comprises, as a first component, a manganese complex of Formula I( ), and, as a second component, a non-manganese complex compound of Formula (I), optionally together with one or more physiologically acceptable carriers and/or excipients, wherein X, R, R, R, and R are as defined herein. Methods for treatment of a pathological condition in a patient, for example, a pathological condition caused by the presence of oxygen-derived free radicals, comprises administering to said patient the first component and the second component.
(Continued)

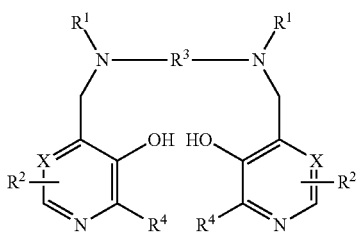

Formula I

41 Claims, 5 Drawing Sheets

(51) Int. Cl.
A61K 33/32 (2006.01)
A61K 45/06 (2006.01)

(58) Field of Classification Search
USPC .......................................................... 514/89
See application file for complete search history.

(56) References Cited

U.S. PATENT DOCUMENTS

| | | | |
|---|---|---|---|
| 6,310,051 | B1 | 10/2001 | Karlsson et al. |
| 6,391,895 | B1 | 5/2002 | Towart et al. |
| 7,351,722 | B2 | 4/2008 | Batteux et al. |
| 2004/0142907 | A1 | 7/2004 | Batteux et al. |
| 2007/0148154 | A1 | 6/2007 | Weill et al. |
| 2010/0298271 | A1 | 11/2010 | Karlsson et al. |

FOREIGN PATENT DOCUMENTS

| | | | | |
|---|---|---|---|---|
| EP | 1060174 B1 | 9/2004 | | |
| EP | 1054670 B1 | 3/2005 | | |
| EP | 1381364 B1 | 8/2006 | | |
| WO | 97/49409 A1 | 12/1997 | | |
| WO | 02/087579 A1 | 11/2002 | | |
| WO | WO 2009/078794 | * | 12/2008 | ............. A61K 31/44 |
| WO | 2009/078794 A1 | 6/2009 | | |

OTHER PUBLICATIONS

Aschner et al ("Manganese and its Role in Parkinson's Disease: From Transport to Neuropathology." Neuromol Med, 2009; 11:252-266).*
Ramesh et al ("TNF-α mediates chemokine and cytokine expression and renal injury in cisplatin nephrotoxicity" J. Clin Invest. 2002, 110(6):835-842).*
Crossgrove et al (NMR Biomed. 2004; 17:544-553).*
(J. G. Cannon, Chapter Nineteen in Burger's Medicinal Chemistry and Drug Discovery, Fifth Edition, vol. I: Principles and Practice, Wiley-Interscience 1995, pp. 783-802).*
Jerome Alexandre et al, Improvement of the Therapeutic Index of Anticancer Drugs by the Superoxide Dismutase Mimic Mangafodipir, Journal of the National Cancer Institute, vol. 98, No. 4, pp. 236-244, Feb. 15, 2006.
Sassia Bedda et al, Mangafodipir prevents liver injury induced by acetaminophen in the mouse, Journal of Hepatology, 39 (2003) pp. 765-772.
Heidi Burok et al, Manganese Dipyridoxyl Diphosphate: MRI Contrast Agent with Antioxidative and Cardioprotective Properties?, Biochemical and Biophysical Research Communications, 254:768-772 (1999).
Janelle Crossgrove et al, Manganese toxicity upon overexposure, NMR in Biomedicine (2004);17:544-553.
Valerie Cizewski Culotta et al, Activation of superoxide dismutases: Putting the metal to the pedal, NIH Public Access Author Manuscript, published as Biochim Biophys Acta. (2006) 1763(7): 747-758.
Salvatore Cuzzocrea et al, Antioxidant Therapy: A New Pharmacological Approach in Shock, Inflammation, and Ischemia/Reperfusion Injury, Pharmacol Rev 53:135-159, 2001.
Doroshow, Redox Modulation of Chemotherapy-Induced Tumor Cell Killing and Normal Tissue Toxicity, Journal of the National Cancer Institute, vol. 98, No. 4, Feb. 15, 2006.
Marcella Folin et al, Zinc content of normal human serum and its correlation with some hematic parameters, BioMetals 1994,7:75-79.
Irwin Fridovich, Oxygen Toxicity: A Radical Explanation, The Journal of Experimental Biology, 201:1203-1209 (1998).
Alan Hazell et al, Alzheimer type II astrocytic changes following sub-acute exposure to manganese and its prevention by antioxidant treatment, Neuroscience Letters, 396 (2006) 167-171.
Hustvedt et al, Plasma Pharmacokinetics, Tissue Distribution and Excretion of MnDPDP in the Rat and Dog After Intravenous Administration, Acta Radiologica, 38 (1997) 690-699.
Karlsson, Antioxidant activity of mangafodipir is not a new finding, Letters to the Editor / Journal of Hepatology, 40 (2004) 869-873.
Karlsson et al, Cardioprotective Effects of the MR Contrast Agent MnDPDP and Its Metabolite MnPLED Upon Reperfusion of the Ischemic Porcine Myocardium, Acta Radiologica, 42 (2001) 540-547.
Karlsson et al, The Magnetic Resonance Imaging Contrast Agent Mangafodipir Exerts Antitumor Activity via a Previously Described Superoxide Dismutase Mimetic Activity, Cancer Res 2006; 66: (1). Jan. 1,2006, p. 598.
King et al, Zinc Homeostasis in Humansl, The Journal of Nutrition (2000), pp. 1360s-1366s.
Laurent et al, Controlling Tumor Growth by Modulating Endogenous Production of Reactive Oxygen Species, Cancer Research, 2005; 65(3):948-956, Feb. 1, 2005.
Muscoli et al, On the selectivity of superoxide dismutase mimetics and its importance in pharmacological studies, British Journal of Pharmacology (2003) 140, 445-460.
Rocklage et al, Manganese(II) N,N'-Dipyridoxylethylenediamine-N,N'-diacetate 5,5'-Bis(phosphate). Synthesis and Characterization of a Paramagnetic Chelate for Magnetic Resonance Imaging Enhancement, Inorganic Chemistry, vol. 28, No. 3:477-485 (1989).
Scheuhammer et al, Influence of Chronic MnCl2 and EDTA Treatment on Tissue Levels and Urinary Excretion of Trace Metals in Rats, Arch. Environm. Contam. Toxicol., 11:515-520 (1982).
Schmidt et al, Stability and transmetallation of the magnetic resonance contrast agent MnDPDP measured by EPR, J Biol Inorg Chem (2002) 7: 241-248.
Skjold et al, Relaxation Enhancing Properties of MnDPDP in Human Myocardium, Journal of Magnetic Resonance Imaging, 20:948-952 (2004).
Southon et al, NMR Relaxation Studies With MnDPDP, Acta Radiologica, 38 (1997) 708-716.
Toft et al, Metabolism and Pharmacokinetics of MnDPDP in Man, Acta Radiologica 38 (1997) 677-689.
Wendland, Applications of manganese-enhanced magnetic resonance imaging (MEMRI) to imaging of the heart, NMR in Biomedicine, 2004;17:581-594.
Yokel, Brain Uptake, Retention, and Efflux of Aluminum and Manganese, Environmental Health Perspectives, vol. 110, Supplement 5, Oct. 2002, 699-704.
Yri et al, Mangafodipir as a cytoprotective adjunct to chemotherapy—a case report, Acta Oncologica, Jan. 2009, 1-3.

* cited by examiner

PHARMACEUTICAL COMPOSITIONS AND THERAPEUTIC METHODS EMPLOYING A COMBINATION OF A MANGANESE COMPLEX COMPOUND AND A NON-MANGANESE COMPLEX FORM OF THE COMPOUND

RELATED APPLICATIONS

The present application is a 371 of PCT/IB2010/053097 filed Jul. 6, 2010 and claims priority under 35 U.S.C. 119 of U.S. Applications Nos. 61/223,204 filed Jul. 6, 2009 and 61/306,348 filed Feb. 19, 2010.

FIELD OF THE INVENTION

The present invention relates to pharmaceutical compositions and therapeutic methods employing a combination of a manganese complex of a dipyridoxyl compound, for example, MnDPDP (Manganese N,N'-bis-(pyridoxal-5-phosphate)-ethylenediamine-N,N'-diacetic acid) or other manganese complexes of Formula I (hereafter Manganese PyridoxyL EthylDiamine derivatives or MnPLED-derivatives), as a first component, and a non-manganese-containing compound of Formula I (hereafter named PLED-derivative), for example DPDP, as a second component, as therapeutic agents. The compositions and methods of the invention may be used in any treatment method conventionally employing such manganese complexes for therapeutic effect. In a specific embodiment, the compositions may be used in the treatment of pathological conditions caused by the presence of oxygen-derived free radicals in the body, i.e., oxidative stress.

BACKGROUND OF THE INVENTION

The use of dipyridoxyl based chelating agents and their metal chelates and certain manganese containing compounds, in particular manganese chelates, in medicine is known. See EP 0910360, U.S. Pat. No. 6,147,094, EP 0936915, U.S. Pat. No. 6,258,828, EP 1054670, U.S. Pat. No. 6,310,051, EP 1060174, and U.S. Pat. No. 6,391,895, for example, which disclose that certain chelating agents, in particular dipyridoxyl and aminopolycarboxylic acid-based chelating agents, and their metal chelates, are effective in treating or preventing anthracycline-induced cardiotoxicity, radiation-induced toxicity, ischemia-reperfusion-induced injuries and atherosclerosis, or from a more general point of view, every pathological condition caused by the presence of oxygen-derived free radicals, i.e., oxidative stress, in humans and animals.

Short-lived but highly reactive oxygen-derived free radicals have long been known to participate in pathological tissue damage, especially during treatment with cytotoxics/cytostatics and radiotherapy in cancer patients (Towart et al., Arch Pharmacol 1998; 358 (Suppl 2):R626, Laurent et al., Cancer Res 2005; 65:948-956, Karlsson et al., Cancer Res 2006; 66:598, Alexandre et al., J Natl Cancer Inst 2006; 98:236-244, Doroshow, J Natl Cancer Inst 2006; 98:223-225), acetaminophen-induced liver failure (Bedda et al., J Hepatol 2003; 39:765-772; Karlsson, J Hepatol 2004; 40:872-873), in ischemic heart disease (Cuzzocrea et al., Pharmacol Rev 2001; 53:135-159) and in various neurodegenerative diseases, including Alzheimer's disease, amyotrophic lateral sclerosis (ALS), Parkinson's disease, and multiple sclerosis (Knight, Ann Clin Lab Sci. 1997; 27:11-25). Overproduction of oxygen-derived free radicals is also implicated in pathological conditions of iron overload (Rachmilewitz et al., Ann N Y Acad Sci. 2005; 1054:118-23), for example, in thalassemia, sickle cell anemia and transfusional hemosiderosis. Oxygen-derived free radicals are also implicated in hepatitis-induced liver cirrhosis (Farrell et al., Anat Rec 2008; 291:684-692) and in noise-induced hearing loss (Wong et al., Hear Res 2010; 260:81-88).

One of the MnPLED-derivatives, namely manganese N,N'-bis-(pyridoxal-5-phosphate)-ethylenediamine-N,N'-diacetic acid (Manganese DiPyridoxyl DiPhosphate; MnDPDP), is approved for use as a diagnostic MRI contrast agent in humans. Interestingly, MnDPDP has also been shown to protect mice against serious side effects of several cytotoxic/cytostatic drugs (doxorubicin, oxaliplatin, 5-fluorouracil and paclitaxel), without interfering negatively with the anticancer effects of these drugs (Towart et al., 1998, Laurent et al., 2005, Karlsson et al., 2006, Alexandre et al., 2006, Doroshow, 2006). MnDPDP has been tested in one colon cancer patient going through palliative treatment with a combination of folinate, 5-fluorouracil and oxaliplatin (FOLFOX) (Yri et al., Acta Oncol. 2009; 48:633-635). The preclinical data and the results from this single patient were so promising that clinical testing in cancer patients has started in Sweden. A first feasibility study has been completed and positive results have been reported to Swedish Medical Agency.

MnDPDP has also been described to protect mice against acetaminophen-induced acute liver failure in mice (ALF) (Bedda et al., 2003; Karlsson, 2004). ALF is characterized by massive hepatocyte cell death, a condition caused by glutathione depletion, oxygen-derived free radicals and mitochondrial damage.

MnDPDP is a pro-drug in the sense that it probably has to be metabolized into N,N'-dipyridoxyl ethylenediamine-N,N'-diacetic acid (MnPLED) before it can exert cytoprotective effects during in vivo conditions (e.g., see Karlsson et al., Acta Radiol 2001; 42:540-547).

Manganese is an essential as well as potentially neurotoxic metal. It has been know for many years that under conditions of chronic exposure to high levels of manganese, a syndrome of extrapyramidal dysfunction similar to Parkinson's syndrome, although clinically a different disease entity, frequently occurs (see Scheuhammer & Cherian, Arch Environm Contam Toxicol 1982; 11:515-520). When a diagnostic MR imaging dose of MnDPDP is intravenously injected into humans, about 80% of the administered manganese is released (Toft et al., Acta Radiol 1997; 38:677-689). Release of paramagnetic manganese is in fact a prerequisite for the diagnostic MR imaging properties of MnDPDP (Wendland, NMR Biomed 2004; 17:581-594). On the other hand, the therapeutic effects of MnDPDP and its dephosphorylated counterparts MnDPMP (N,N'-dipyridoxylethylenediamine-N,N'-diacetate-5-phosphate) and MnPLED depend on the intact metal complex (Brurok et al., Biochem Biophys Res Commun. 1999; 254:768-721, Karlsson et al 2001; 42:540-547).

PLED-derivatives mimic the mitochondrial enzyme manganese superoxide dismutase (MnSOD) (Brurok et al., 1999). MnSOD protects the mammalian cell from the superoxide radical, a byproduct from oxygen metabolism, which is produced in fairly high amounts during normal aerobic conditions; no mammalians survive without a functional MnSOD. MnSOD has the fastest turnover number (reaction rate with its substrate) of any known enzyme ($>10^9 M^{-1} s^{-1}$) (Fridovich, J Exp Biol. 1998; 201:1203-1209). Low molecular weight MnSOD mimetics may have turnover rates close to that of native MnSOD (Cuzzorea et al., 2001). Interestingly, physiological buffers containing transition metals like manganese may have similar high turnover numbers (Culotta et al., Biochim Biophys Acta. 2006; 1763:747-758). However, the importance of native SOD enzymes is consistent with a selection process favoring organisms that elaborate a means of localizing transition metal catalyst for superoxide dismutation to parts of the cell where there is a high need for such dismutation, e.g., mitochondria. Furthermore, results from myocardial ischemia-reperfusion in anaesthetized pigs inevitably show that the intact MnPLED, but not manganese per se, protects against oxidative stress, seen as reduction in infarct size (Karlsson et al., 2001). Effective inactivation of superoxide is essential in preventing generation of very devastating hydroxyl radicals and peroxynitrite (Cuzzocrea et al., 2001). During pathological oxidative stress, the formation of superoxide radicals often exceeds the endogenous capacity for inactivation. Furthermore, superoxide stimulates production of peroxynitrite which nitrates endogenous SOD. Once nitrated, MnSOD and/or CuZn SOD lose their enzymatic activity, an event favoring the accumulation of superoxide and superoxide-driven damage (Muscoli et al., Br J Pharmacol 2003; 140: 445-460). Exogenous addition of MnPLED-derivatives may in such situations re-establish the protective potential. PLED-derivatives are in addition strong iron binders, as described in EP 1054670, U.S. Pat. No. 6,310,051 and by Rocklage et al., (Inorg Chem 1989; 28:477-485), and some MnPLED-derivatives may have catalase and glutathione reductase activities (Laurent et al., 2005), which may further increase their antioxidant capacity.

For diagnostic imaging use and other sporadic use, dissociation of manganese from MnDPDP represents no major toxicological problem. Due to uptake into CNS, however, for more frequent use, for example in therapeutic methods, accumulated manganese toxicity may represent a serious neurotoxicological problem (Crossgrove & Zheng, NMR Biomed. 2004; 17:544-53). Thus, for more frequent therapeutic use, compounds that readily dissociate manganese should be avoided.

In order for manganese to distribute from blood into brain tissue, it must cross either the blood-brain barrier or the blood-cerebrospinal fluid barrier. The mechanism by which manganese is taken up by the brain is poorly understood. However, some references suggest that manganese is taken up as a free ion ($Mn^{2+}/Mn^{3+}$) or as manganese citrate and support the hypothesis that manganese transport is facilitated by either an active or a passive mechanism (Rabin et al., J Neurochem. 1993; 61:509-517; Yokel, Environ Health Perspect 2002; 110 suppl 5:699-704). Manganese may also be transported into CNS bound to transferrin. Nevertheless, in the case of MnDPDP and its dephosphorylated counterparts (in addition to other MnPLED-derivatives), manganese must probably dissociate from its corresponding chelator DPDP, DPMP or PLED (or other PLED-derivatives) to gain access into the brain.

Treatment with the metal chelator EDTA in rats who have previously been systemically exposed to manganese for many days considerably increased urinary excretion of manganese (Scheuhammer & Cherian, 1982) Similar effects of EDTA have also been seen on urine concentration of manganese in chronically poisoned welders (see Crossgrove & Zheng, 2004). Treatment of rats with manganese (II) chloride (50 mg/kg body weight, i.p.) once daily for 1 or 4 days led to increases in manganese levels of up to 232, 523, and 427% in the cerebral cortex, globus pallidus, and cerebellum, respectively. These changes were accompanied by development of pathological changes in glial morphology. Co-treatment with the manganese chelator 1,2-cyclohexylenedinitrilotetraacetic (CDTA) completely blocked this pathology (see Hazell et al., Neurosci Lett. 2006; 396:167-71), although these authors did not report if this effect of CDTA was due to direct inhibition of manganese uptake into the brain.

Thus, while manganese complex compounds are known for providing therapeutic effects in various treatments, there is a need to develop means for obtaining such therapeutic effects while reducing the undesirable side effects associated with such treatments.

SUMMARY OF THE INVENTION

The present invention provides improved pharmaceutical compositions and therapeutic methods for treatment of pathological conditions in a human or a non-human patient, and particularly provides such pharmaceutical compositions and therapeutic methods which overcome various disadvantages of the prior art. The pharmaceutical compositions and methods may be employed in any therapeutic environment for which a manganese complex of Formula I as defined herein is effective. In a specific embodiment, the pharmaceutical compositions and methods may be employed in a therapeutic environment to treat a condition caused by the presence of oxygen-derived free radicals, i.e., oxidative stress.

In one embodiment, the invention is directed to pharmaceutical compositions for treatment of a pathological condition in a patient, comprising, as a first compound, a manganese complex of Formula I, and, as a second component, a non-manganese complex compound of Formula I, optionally together with one or more physiologically acceptable carriers and/or excipients,

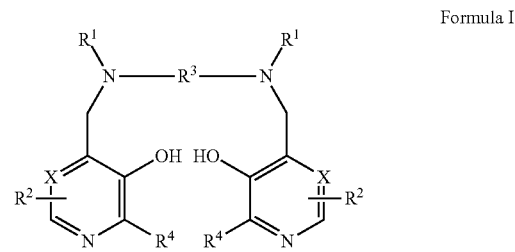

Formula I wherein
X represents CH or N,
each $R^1$ independently represents hydrogen or —$CH_2COR^5$;
$R^5$ represents hydroxy, optionally hydroxylated alkoxy, amino or alkylamido;
each $R^2$ independently represents $ZYR^6$ wherein Z represents a bond or a $C_{1-3}$ alkylene or oxoalkylene group optionally substituted by $R^7$;
Y represents a bond, an oxygen atom or $NR^6$;
$R^6$ is a hydrogen atom, $COOR^8$, alkyl, alkenyl, cycloalkyl, aryl or aralkyl, group optionally substituted by one or more groups selected from $COOR^8$, $CONR^8_2$, $NR^8_2$, $OR^8$, =$NR^8$, =O, $OP(O)(OR^8)R^7$ and $OSO_3M$; $R^7$ is hydroxy, optionally hydroxylated, optionally alkoxylated alkyl or aminoalkyl group;
$R^8$ is a hydrogen atom or an optionally hydroxylated, optionally alkoxylated alkyl group;
M is a hydrogen atom or one equivalent of a physiologically tolerable cation;

R³ represents a C₁₋₈ alkylene, a 1,2-cykloalkylene, or a 1,2-arylene group, optionally substituted with R⁷; and
each R⁴ independently represents hydrogen or C₁₋₃ alkyl.

In another embodiment, the invention is directed to methods for treatment of a pathological condition in a patient, including, but not limited to, a pathological condition caused by the presence of oxygen-derived free radicals. The methods comprise administering to the patient the first component and the second component as described above, for example in a pharmaceutical composition according to the invention.

The pharmaceutical compositions and methods of the present invention have surprising advantages, as disclosed and demonstrated herein. For example, the compositions and methods can increase the amount of excreted manganese, reduce the amount of free manganese in the patient, and/or increase the amount of therapeutic metabolite produced in vivo, as compared with the effects obtained by administration of the first manganese complex component only, in the absence of the second non-manganese-containing component. Additional advantages and embodiments of the inventive pharmaceutical compositions and methods will be more fully understood in view of the following detailed description.

BRIEF DESCRIPTION OF THE DRAWINGS

The following Detailed Description will be more fully understood in view of the drawings, wherein:

(FIG. 1A) or as percentage of the injected dose (FIG. 1B); mean±S.E.M.; n=7 in each group.

(FIG. 3A) and as percentage increase in brain Mn (FIG. 3B); mean±S.E.M.; n=5 in each group.

(FIG. 4B); mean±S.E.M.; n=2 in each group.

Figure 1A:
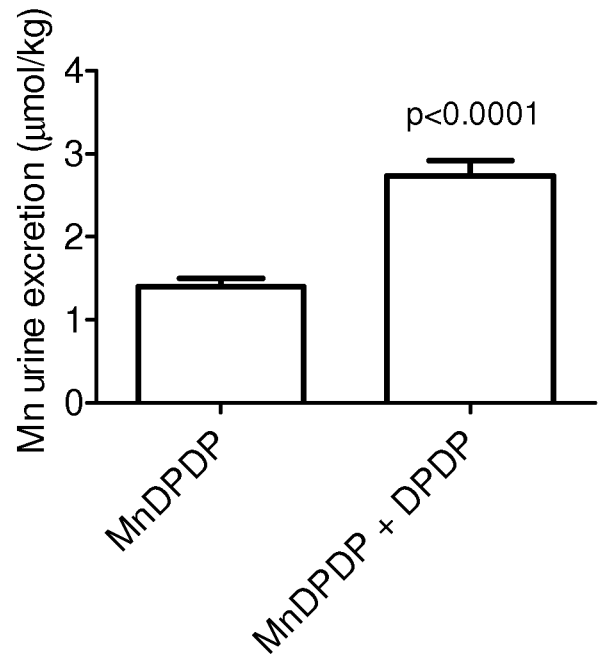
FIGS. 1A and 1B show the Mn content in 0-24 h urine from rats injected with MnDPDP alone or with a combination of MnDPDP and DPDP, expressed as µmol/kg b.w.

The drawings will be more fully understood in view of the Examples.

DETAILED DESCRIPTION

The present invention is directed to pharmaceutical compositions and therapeutic methods employing a combination of, as a first component, a manganese complex of Formula I as set forth herein and, as a second component, a non-manganese complex compound of Formula I. The compounds of formula I are dipyridoxyl compounds and are referred to herein as PLED (PyridoxyL EthylDiamine)-derivatives although it is recognized that the derivatives also act as pro-drugs of PLED as they can metabolize to form PLED in vivo. Such compounds in the form of metal complexes are referred to as MetalPLED-derivatives, i.e., MnPLED-derivatives, and MetalPLED chelators.

The present pharmaceutical compositions employ, as a first component, a manganese complex of Formula I, and, as a second component, a non-manganese complex compound of Formula I:

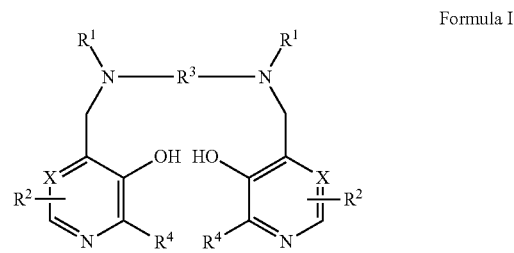

Formula I wherein
X represents CH or N,
each R¹ independently represents hydrogen or —CH₂COR⁵;
R⁵ represents hydroxy, optionally hydroxylated alkoxy, amino or alkylamido;
each R² independently represents ZYR⁶ wherein Z represents a bond or a C₁₋₃ alkylene or oxoalkylene group optionally substituted by R⁷;
Y represents a bond, an oxygen atom or NR⁶;
R⁶ is a hydrogen atom, COOR⁸, alkyl, alkenyl, cycloalkyl, aryl or aralkyl, group optionally substituted by one or more groups selected from COOR⁸, CONR⁸₂, NR⁸₂, OR⁸, =NR⁸, =O, OP(O)(OR⁸)R⁷ and OSO₃M; R⁷ is hydroxy, optionally hydroxylated, optionally alkoxylated alkyl or aminoalkyl group;
R⁸ is a hydrogen atom or an optionally hydroxylated, optionally alkoxylated alkyl group;
M is a hydrogen atom or one equivalent of a physiologically tolerable cation;
R⁸ represents a C₁₋₈ alkylene, a 1,2-cykloalkylene, or a 1,2-arylene group, optionally substituted with R⁷; and
each R⁴ independently represents hydrogen or C₁₋₃ alkyl.

In a specific embodiment, R⁵ is hydroxy, C₁₋₈ alkoxy, ethylene glycol, glycerol, amino or C₁₋₈ alkylamido; Z is a bond or a group selected from CH₂, (CH₂)₂, CO, CH₂CO, CH₂CH₂CO and CH₂COCH₂; Y is a bond; R⁶ is a mono- or poly(hydroxy or alkoxylated)alkyl group or of the formula OP(O)(OR⁸)R⁷; and R⁷ is hydroxy, or an unsubstituted alkyl or aminoalkyl group. In a further embodiment, R³ is ethylene and each group R¹ represents —CH₂COR⁵ in which R⁵ is hydroxy. In still further embodiments, the first component is manganese N,N'-bis-(pyridoxal-5-phosphate)-ethylenediamine-N,N'-diacetic acid or a salt thereof (MnDPDP) and the second component is N,N'-bis-(pyridoxal-5-phosphate)-ethylenediamine-N,N'-diacetic acid (DPDP) or a salt or non-manganese complex thereof. In more specific embodiments, the second component is DPDP, calcium DPDP (CaDPDP) or magnesium DPDP (MgDPDP), or a combination of two or more thereof.

In additional embodiments of the invention, the first component has a $K_a$ value in the range of from $10^8$ to $10^{24}$. In a further embodiment, the second component has a lower $K_a$ value for $Mn^{2+}$ than the corresponding $K_a$ value for zinc ($Zn^{2+}$), by a factor of at least 10.

The first component and the second component may be employed in varying amounts as will be discussed in further detail hereafter. It is only necessary that there is manganese-free compound, in addition to the manganese containing compound, i.e., a "surplus" of the non-complexed derivative compound. However, in a specific embodiment, the second component is included in an equimolar or greater amount relative to the first component. In another embodiment, the second component is included in a greater amount on a molar basis relative to the first component. In a more specific embodiment, the first component and the second component are included in a first component:second component molar ratio in the range of about 1:1 to 1:20, 1:1 to 1:10, or 1:1 to 1:5. In an even more specific embodiment, the first component and the second component are included in a first component:second component molar ratio in the range of about 1:2 to 3:4. In a specific embodiment, for example for cancer treatment, an amount of the first component, for example MnDPDP, may be 10 mM MnDPDP, and the amount of the second component, for example DPDP, may be 50 mM DPDP, 0.2 ml/kg will result in a dose of 2 µmol/kg b.w. MnDPDP+10 µmol/kg b.w. DPDP, providing a molar ratio of 1:5. In additional embodiments, the dose of Mn-containing compound such as MnDPDP can be lowered. If the MnDPDP dose is lowered, a ratio smaller than 1:5 may be employed.

In vivo-release of manganese from MnPLED-derivatives, including Manganese N,N'-bis-(pyridoxal-5-phosphate)-ethylenediamine-N,N'-diacetic acid (MnDPDP), depends on the presence of free or readily dissociable zinc in the body. Zinc has about 1000 times higher affinity than manganese for DPDP or its dephosphorylated counterparts (Rocklage et al., 1989). Experimental studies suggest that manganese release in vivo saturates when the dose of MnDPDP is increased about two to four times the diagnostic imaging dose of 5 to 10 µmol/kg (Southon et al., Acta Radiol. 1997; 38:708-716). Cardiac and liver imaging with MnDPDP in healthy volunteers indicates a saturation dose at 10 to 20 µmol/kg in man (Skjold et al., J. Magn. Reson. Imaging 2004; 20:948-952, Toft et al., 1997).

It has been discovered according to the invention, that, surprisingly, addition of surplus non-manganese-containing PLED derivative, for example DPDP, to an MnPLED-derivative therapy, for example MnDPDP therapy, protects MnDPDP from releasing neurotoxic manganese. Although the mechanism behind manganese uptake into the brain is not entirely understood, as pointed out above, surplus of the non-manganese-containing PLED derivative such as DPDP administered in combination with the manganese-containing PLED derivative such as MnDPDP significantly reduces the uptake of manganese to the brain. Low molecular weight manganese chelates, like MnPLED-derivatives, and their Zn-counterparts will readily be excreted through the kidney, governed by the glomerulus filtration rate (GFR), whereas manganese not bound to a low molecular weight chelator will be retained for quite a while in the body and excreted slowly and mainly via the biliary route (Toft et al., 1997). While not wishing to be bound by theory, it is believed that the combination according to the invention maintains the MnPLED chelator form, whereby increased amounts of chelates are available for excretion and the amount of free Mn for uptake into the brain is reduced.

In one embodiment of the methods according to the invention, Mn excretion, i.e., in urine, is increased by at least about 100% (see the following Example 1), by combining administration of a manganese complex of a dipyridoxyl compound, i.e., the first component, with the administration of a non-manganese dipyridoxyl compound, i.e., the second component. Example 1 shows that excretion of manganese into the urine increases from 1.41 µmol/kg to 2.73 µmol/kg, i.e., about 100%. However at lower and maybe more therapeutic relevant doses of MnDPDP (the recently completed Swedish feasibility clinical study in cancer patient employed 2 µmol/kg), from Example 4 the relative increase is expected to be considerably higher. In additional embodiments, the Mn excretion is increased by at least about 200% or by at least 300%, all on a molar basis, by combining administration of a manganese complex of a dipyridoxyl compound, i.e., the first component, with the administration of a non-manganese dipyridoxyl compound, i.e., the second component. In further embodiments, the Mn excretion is increased by at least about 400%, or by at least about 500%, all on a molar basis, by combining administration of a manganese complex of a dipyridoxyl compound, i.e., the first component, with the administration of a non-manganese dipyridoxyl compound, i.e., the second component. Thus, in a specific embodiment, the present invention solves the neurotoxicological problem of MnDPDP, or its dephosphorylated counterparts, during more frequent use by adding a surplus of DPDP, or its dephosphorylated counterparts, to the formulation.

A further advantage results as the therapeutic chelator form is maintained at an increased level, so that a lower dosage of the chelate may be administered in the combination to obtain the same therapeutic effect as a greater dosage of chelate administered alone, i.e., in the absence of the non-manganese-containing compound.

When a clinical dose of and MnPLED-derivative such as MnDPDP (i.e., 5-10 µmol/kg b.w., intravenous administration) is used as an MRI contrast agent in a human, more than 80% of the manganese bound to DPDP is displaced by zinc (Toft et al., 1997). As smaller doses of MnDPDP are administered, the percentage of manganese which dissociates will be even greater as will be discussed below. MnDPDP behaves in that perspective in a similar manner in rats and dogs (Hustvedt et al., Acta Radiol. 1997; 38:690-699); however, almost all manganese in MnDPDP is displaced by zinc when the compound is administered to pigs and is hence without cytoprotective effects in pigs (Karlsson et al., 2001). Displacement of manganese is a prerequisite and therefore desirable for use as an MRI contrast agent, as discussed above. However, the intact manganese complex MnPLED-derivative, for example MnDPDP and its dephosphorylated counterparts, is necessary for obtaining the therapeutic effect, for example, against various form of oxidative stress (Brurok et al., 1999; Karlsson et al., 2001). For example, whereas in vivo administration of MnDPDP protects against various oxidative stressors, e.g., ischemia-reperfusion, cytotoxic/cytostatic drugs and acetaminophen intoxication, it does not protect the pig heart against ischemia-reperfusion-induced myocardial infarction (Karlsson et al., 2001), from which it may be concluded that the in vivo cytoprotective effects of MnDPDP are an inherent property of the intact manganese complex.

The addition of the non-manganese complex compound such as DPDP to stabilize a manganese compound such as MnDPDP or its dephosphorylated counterparts from releasing manganese according to the invention thus provides another important advantage, namely increased therapeutic efficacy. For example, when a clinically relevant imaging dose of MnDPDP (5-10 µmol/kg) is intravenously injected, more than 80% of the manganese originally bound to DPDP is released, contributing to the imaging efficacy. Consequently less than 20% remains bound to DPDP or its dephosphorylated counterparts, contributing to the therapeutic activity of MnDPDP. When, according to the present invention, as exemplified by Example 1, the amount of manganese which is released from the complex is reduced, from 85% to 70% by addition of DPDP to the administered MnDPDP, about 30% of the injected dose of MnDPDP will contribute to the therapeutic activity, thereby doubling the amount of Mn-chelate available for therapeutic effect. Where the release of manganese is so mainly governed by the added DPDP, this means that the dose of MnDPDP in the presence of the added DPDP can be reduced by 50% for an equipotent therapeutic effect. However, as discussed below, at lower and, in certain embodiments, more therapeutic relevant doses of MnDPDP, the effects of added DPDP will even be more accentuated. This in turn means that the addition of DPDP to MnDPDP will have a profound effect on the toxicological potential of MnDPDP.

Zinc is present in all body tissues and fluids. The total body zinc content in humans has been estimated to be 2-3 g (Folin et al., BioMetals 1994; 7:75-79). Plasma zinc represents about 0.1% of total body zinc content, and it is mainly this small fraction of zinc that competes with manganese for binding to DPDP or its dephosphorylated counterparts, DPMP and PLED, after administration. The human body has a very high capacity to maintain zinc homeostasis through synergistic adjustments in gastrointestinal absorption and excretion (King et al., J Nutr 2000; 130:1360S-1366S). There is therefore no or a very low risk that repeated injection of clinically relevant doses of MnDPDP, containing surplus of DPDP, should induce zinc deficiency. In case of any tendency of zinc deficiency, such problem can be easily solved by dietary zinc supplementation between MnDPDP administrations.

From preclinical work (Southon et al., 1997) and from clinical work (Skjold et al., 2004), it is reasonable to assume that the body contains 10 to 20 μmol/kg body weight (b.w.) zinc that is readily exchangeable for manganese in a MnPLED-derivative such as MnDPDP. This substantially corresponds with the zinc content of the plasma (see above). The PLED-derivatives such as DPDP contain one binding site for manganese/zinc per molecule. Thus, in view of the 1000 times higher affinity for zinc to the chelator, in one embodiment of the invention, the addition of the non-manganese-containing compound such as DPDP in a dose of 1 to 100 μmol/kg b.w. to a MnPLED-derivative formulation such as an MnDPDP formulation will protect from release of manganese after administration to a patient.

Preclinical work demonstrates that intravenously administered doses in a range of 1 to 30 μmol/kg b.w. of MnDPDP reduce doxorubicin-induced cardiomyopathy in mice and myocardial infarction in pigs (see EP 0910360, U.S. Pat. No. 6,147,094, EP 0936915, U.S. Pat. No. 6,258,828, Karlsson et al., 2001; Towart et al., 1998). Other MnPLED-derivatives display efficacy at different dose levels, and doses of 10 to 100 times lower than the aforementioned dose interval are within the scope of the pharmaceutical compositions and methods of the present invention (EP 0910360, U.S. Pat. No. 6,147,094). Taking into in consideration differences between species, differences in efficacy between various MnPLED-derivatives, differences in body surface and various administration routes, a suitable dose for the first component according to a specific embodiment of the invention, when administered to a patient will be in the range of about 0.01 to 10 μmol/kg b.w., and a suitable dose for the second component according to a specific embodiment of the invention will be in the range of about 1 to 100 μmol/kg b.w. In a more specific embodiment, the second component is administered in an equimolar or greater amount relative to the first component and is in the range of about 1 to 20 μmol/kg b.w. In yet a further specific embodiment, the first component is administered in an amount of about 1 to 2 μmol/kg b.w.

The pharmaceutical composition can be a ready-to-use formulation containing both the first component, i.e., the Mn-PLED-derivative, and the second component, i.e., the PLED-derivative, or the pharmaceutical composition may comprise the first component and the second component in separate but associated packages for administration in combination. In this regard, the first component and the second component may be administered in combination or separately, simultaneously or sequentially.

Optionally, the pharmaceutical compositions of the present invention may include one or more physiologically acceptable carriers and/or excipients, in a manner well-known to those skilled in the art. In one embodiment, the compounds of Formula I may for example be suspended or dissolved in an aqueous medium, optionally with the addition of pharmaceutically acceptable excipients. Suitable excipients for the pharmaceutical compositions include any conventional pharmaceutical or veterinary formulation excipients, including, but not limited to, stabilizers, antioxidants, osmolality adjusting agents, buffers, pH adjusting agents, binders, fillers, and the like. The pharmaceutical compositions may be in a form suitable for administration, including but not limited to parenteral or enteral administration. In a specific embodiment, the composition is in a form suitable for example injection or infusion. Thus, the pharmaceutical compositions of the present invention may be in a conventional pharmaceutical administration form such as a tablet, capsule, powder, solution, suspension, dispersion, syrup, suppository, or the like.

The pharmaceutical compositions according to the present invention may be administered by various routes, for example orally, transdermally, rectally, intrathecally, topically or by means of inhalation or injection, in particular subcutaneous, intramuscular, intraperitoneal or intravascular injection. Other routes of administration may be used as well, including intratympanic, and routes which increase the effectiveness, the bioavailability or the tolerance of the products are preferred. The most appropriate route can be chosen by those skilled in the art according to the particular formulation which is used.

As indicated, the compositions may be administered for therapeutic treatment of a pathological condition in a patient, and particularly in any method in which the Mn complex is known for use. In a specific embodiment, the compositions may be administered for therapeutic treatment of a pathological condition in a human patient or another mammal. In another specific embodiment, a composition according to the invention is administered for treatment of a pathological condition caused by the presence of oxygen-derived free radicals, i.e., oxidative stress. In one embodiment, the pharmaceutical compositions are employed in cytotoxic or cytostatic drug treatment, wherein the MnPLED-derivative is administered to provide protection from disadvantageous side effects of the cytotoxics/cytostatic drugs, for example, in cancer patients. In a more specific embodiment, the cytotoxic or cytostatic drug comprises at least one of doxorubicin, oxaliplatin, 5-fluorouracil or paclitaxel. The methods according to the invention may also include, but are not limited to, treatment of acetaminophen-induced liver failure, ischemic heart disease, including ischemia-reperfusion-induced injury, or myocardial ischemia-reperfusion-induced injury, both in an acute as well as elective setting, a condition associated with a thrombolytic treatment, a cardiopulmonary bypass, or percutaneous transluminal angioplasty, or is a result of cardiac or organ transplantation surgery, iron overload, for example, thalassemia, sickle cell anemia or transfusional hemosiderosis, hepatitis-induced liver cirrhosis, radiation induced injury, for example, resulting from radiation therapy, various neurodegenerative diseases, including Alzheimer's disease, amyotrophic lateral sclerosis (ALS), Parkinson's disease, and multiple sclerosis, and the like.

Various embodiments of aspects of the pharmaceutical compositions and therapeutic methods of the invention are demonstrated by the following Examples.

Example 1

This example measures Mn urine excretion in animals receiving MnDPDP alone and animals receiving MnDPDP and DPDP.

Method

Fourteen male Wistar rats (approximately 250 g) were injected intravenously, via one of the tail veins, with 0.25 ml of a 10 mM MnDPDP formulation (Teslascan™, mangafodipir, GE Healthcare). Seven of these rats received only the MnDPDP (MnDPDP), whereas 7 other rats received, in addition to MnDPDP, 0.5 ml of a 10 mM DPDP formulation (MnDPDP+DPDP). After injection, the rats were immediately placed in metabolic cages for urine collection over a period of 0-24 hours. To obtain basal content of manganese (Mn) in urine, two additional (control) rats were placed in metabolic cages for urine collection over the same period of time. The urine samples were then stored at −80° C. until Mn analysis. Before analysis, the samples were thawed and extensively shaken to obtain homogenous samples. A five ml aliquot was taken from each sample and 5 ml concentrated nitric acid was added. The samples were then resolved in a microwave oven and thereafter diluted with distilled water to a final volume of 50 ml. The Mn content of each sample was analyzed by ICP-MS (Inductively Coupled Plasma Mass Spectrometry). An identical sample of MnDPDP as the one injected in the rats (i.e., 0.5 ml) was withdrawn and injected into a test tube. This sample was treated in an identical manner to that of the urine samples and analyzed for its Mn content. Results are presented as total 0-24 h urine Mn content (expressed as μmol/kg±S.E.M.) and as percentage (±S.E.M.) of the injected dose. The statistical difference between animals receiving MnDPDP alone and animals receiving MnDPDP and DPDP, with respect to excretion of manganese into the urine, was tested by an unpaired Student's t-test. A p-value lower than 0.05 was considered as a statistically significant difference.

Results

Figure 1B:
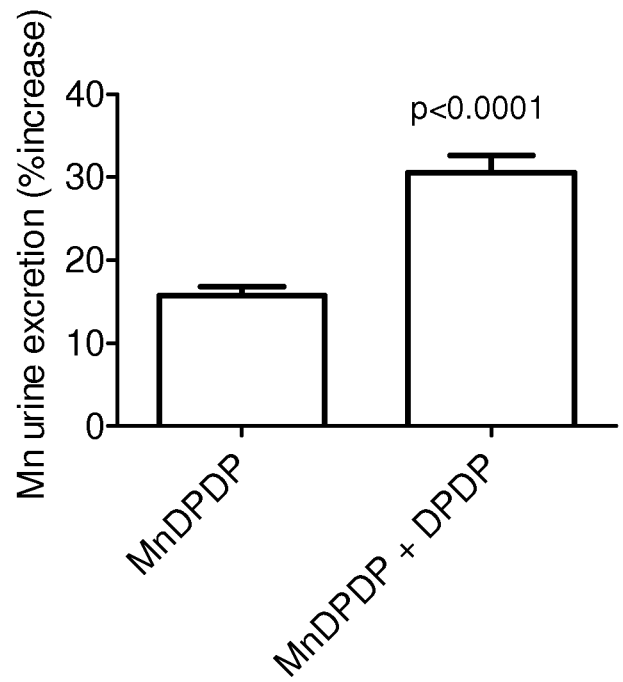

Results are set forth in FIGS. 1A and 1B. The 0.25 ml MnDPDP sample, equivalent to the injected MnDPDP dose, contained 2.24 μmol Mn, corresponding to a dose of 8.96 μmol/kg b.w. in a 250 g rat. The 0-24 h urine from the 2 control rats contained 0.49e5 and 0.357 μmol (Mn)/kg b.w., respectively (mean=0.426 μmol/kg b.w.). The 0-24 h urine minus basal level (0.426 μmol/kg b.w.) from rats injected with MnDPDP alone contained 1.41±0.10 μmol/kg b.w, whereas the urine from rats injected with MnDPDP plus DPDP contained a significantly higher amount Mn, 2.73±0.18 μmol/kg b.w. (FIG. 1A). These values correspond to 15.7±1.1% and 30.5±2.0% excretion in urine during 0-24 h (FIG. 1B). Thus, addition of DPDP doubled Mn excretion in urine. The percentage Mn excreted in urine during 0-24 h after intravenous injection of MnDPDP alone corresponds very well with previously reported figures in rats (Hustvedt et al., Acta Radiol 1997; 38:690-699) and humans (Toft et al., 1997). The present results demonstrate that addition of DPDP stabilizes MnDPDP from releasing Mn under in vivo conditions. This provides several significant advantages in that the amount of free Mn available for uptake by the brain is reduced and the therapeutic index of MnDPDP is increased as more of the therapeutic MnDPDP is available in vivo. Thus, the compositions and methods of the invention render MnPLED-derivative treatment considerably less toxic and more.

Example 1 shows that Mn excretion increases from about 15% (of the given dose 10 μmol/kg b.w. MnDPDP) to about 30% by the addition of DPDP, corresponding to about a 100% increase. At a lower MnDPDP dose, for example, 2 μmol/kg b.w., the relative increase is expected to be much higher because a greater percentage of the Mn is expected to be displaced in the absence of DPDP. That is, in an intravenous administration dose of 10 μmol/kg b.w., about 80% of the manganese bound to DPDP is displaced by zinc (Toft et al., 1997). As smaller doses of MnDPDP are administered, such as 1-2 μmol/kg b.w., the percentage of manganese which dissociates is even greater as the plasma zinc is present at a relative concentration high enough for "displacing" almost all Mn bound to DPDP at such a low dose. This dissociation is illustrated as follows:

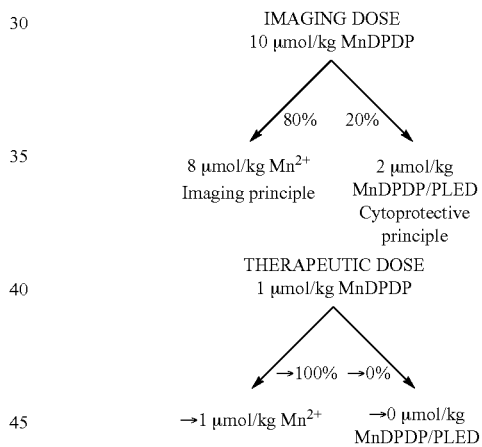

Thus the relative increase in Mn excretion obtained by addition of DPDP is expected to be much higher than 100%. Such a potentiating effect of surplus DPDP at lower doses of MnDPDP is indeed significant and surprising. This benefit is similarly realized by the combination of other MnPLED-derivatives and PLED-derivatives.

Example 2

This example measures Mn brain content in animals receiving MnDPDP alone and animals receiving MnDPDP and DPDP.

Method

Eight male Wistar rats (approximately 250 g) were injected intravenously, via one of the tail veins, with 0.25 ml of a 10 mM MnDPDP formulation (Teslascan™). Four of these rats received only MnDPDP (MnDPDP), whereas 4 other rats received, in addition to MnDPDP, 0.5 ml of a 10 mM DPDP formulation (MnDPDP+DPDP). To obtain the basal content of manganese (Mn) in the rat brain, two additional (control) rats were run in parallel. Twenty-four hours later, the rats were killed and the brains were dissected out and stored at −80° C. until Mn analysis. Before analysis, each brain was resolved in 5 ml concentrated nitric acid plus 3 ml distilled water in a microwave oven, and thereafter diluted with distilled water to a final volume of 50 ml. The Mn content of each sample was analyzed by ICP-MS. Results are expressed as µg/g brain wet weight and percentage increase in Mn brain content.

Results

Figure 2:
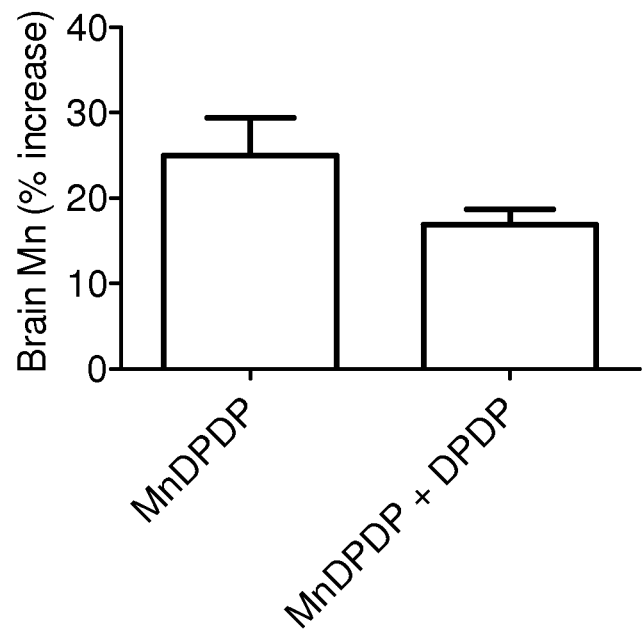
FIG. 2 shows the brain Mn content in rats injected with MnDPDP alone or with a combination of MnDPDP and DPDP, expressed as percentage increase in brain Mn/g w.w.; mean±S.E.M.; n=4 in each group.

Results are set forth in FIG. 2. The Mn brain content in the 2 control rats were 0.40 and 0.39 µg/g brain wet weight, respectively. The Mn content in brain from rats that have received non-supplemented MnDPDP increased by 25.0%, whereas the Mn content in brain increased by 16.9% in rats that had received DPDP-supplemented MnDPDP (FIG. 2). The reduction in Mn uptake in the brain provided by the present invention is significant and surprising.

Example 3

This example measures Mn and Zn brain content in animals receiving MnDPDP alone and animals receiving MnDPDP and DPDP.

Method

Ten male Wistar rats (approximately 250 g) were injected intraperitoneally (i.p.) with 0.25 ml of a 10 mM MnDPDP formulation (Teslascan™). Five of these rats received only MnDPDP (MnDPDP), whereas 5 other rats received, in addition to MnDPDP, 0.5 ml of a 10 mM DPDP formulation (MnDPDP+DPDP). To obtain the basal content of manganese (Mn) in the rat brain, two additional (control) rats were run in parallel in the experiments described in Example 2. Twenty-four hours later, the rats were killed and the brains were dissected out and stored at −80° C. until Mn analysis. In 3 of the rats receiving MnDPDP alone and in 3 rats receiving MnDPDP plus DPDP, the content of brain Zn was also analyzed. Before analysis, each brain was resolved in 5 ml concentrated nitric acid plus 3 ml distilled water in a microwave oven, and thereafter diluted with distilled water to a final volume of 50 ml. The Mn and Zn content of each sample was analyzed by ICP-MS. Results are expressed as µg/g brain wet weight±S.E.M and percentage increase in Mn brain content. Statistical difference between animals receiving MnDPDP alone and animals receiving MnDPDP plus DPDP, with respect to increase in Mn brain content, was tested by an unpaired Student's t-test. A p-value lower than 0.05 was considered as a statistically significant difference.

Results

Figure 3A:
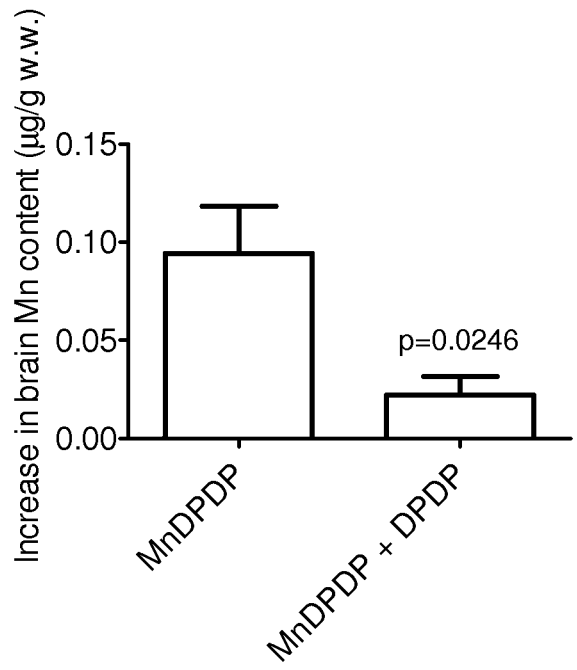
FIGS. 3A and 3B show the brain Mn content in rats injected with MnDPDP alone or with a combination of MnDPDP and DPDP, expressed as increase in µg brain Mn/g w.w.
Figure 3B:
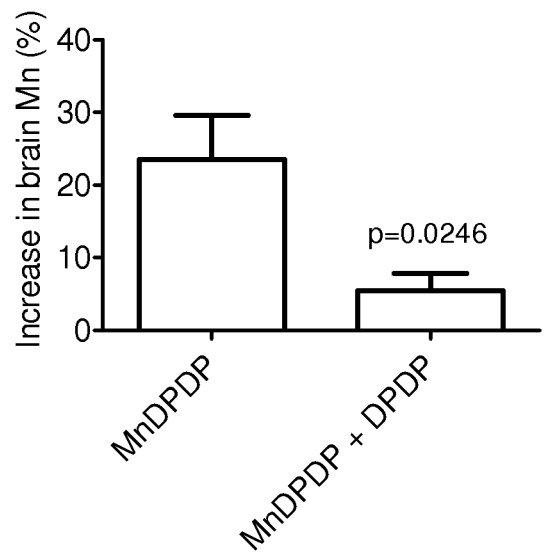
Figure 3C:
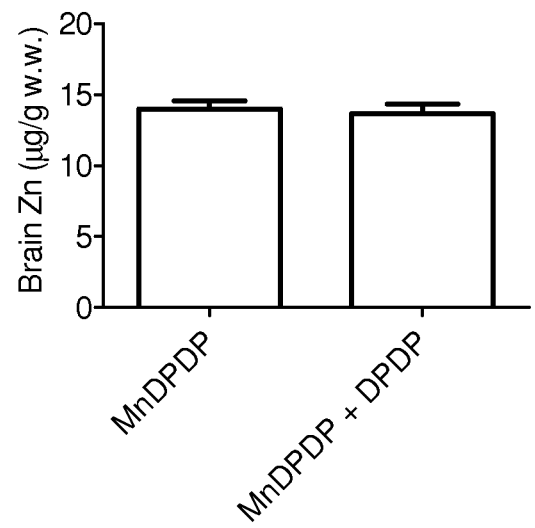
FIG. 3C shows brain Zn content in rats injected with MnDPDP alone or with MnDPDP plus DPDP; mean±S.E.M.; n=3 in each group.

Results are set forth in FIGS. 3A-3C. The Mn brain content in the 2 control rats were 0.40 and 0.39 µg/g w.w., respectively (from Example 2). The Mn content in brain from rats that had received MnDPDP only increased by 0.094±0.024 µg/g w.w., whereas the content increased by only 0.022±0.01 µg/g w.w. in rats that had received DPDP-supplemented MnDPDP (FIG. 3A), corresponding to increases of 23.5 and 5.5%, respectively (FIG. 3B). The Zn brain content in rats receiving MnDPDP alone and in rats receiving MnDPDP+DPDP was identical (FIG. 3C). The present results demonstrate that the addition of a surplus of DPDP reduces uptake of Mn into the brain by more than 75%.

Example 4

This example measures Mn and Zn urine excretion in animals receiving increasing doses of DPDP and animals receiving MnDPDP alone or in combination with DPDP.

Method 10 male Wistar rats (approximately 250 g) were injected intravenously, via one of the tail veins, with either 0, 0.125, 0.250, 0.500 or 0.750 ml of a 10 mM DPDP formulation, corresponding to 0, 5, 10, 20 and 30 µmol/kg b.w. Four other rats received intravenously either 0.250 ml of MnDPDP (10 mM), corresponding to 10 µmol/kg, alone, or in combination with 0.500 ml DPDP (10 mM), corresponding to 20 µmol/kg b.w. After injection, the rats were immediately placed in metabolic cages for urine collection over a period of 0-24 hours. The urine samples were then stored at −80° C. until Zn and Mn analyses. Before analyses, the samples were thawed and extensively shaken to obtain homogenous samples. A five ml aliquot was taken from each sample and 5 ml concentrated nitric acid was added. The samples were then resolved in a microwave oven and thereafter diluted with distilled water to a final volume of 50 ml. The zinc (Zn) and manganese (Mn) content of each sample were analyzed by ICP-MS. Results are presented as total 0-24 h urine Zn and Mn content (expressed as µmol/kg b.w.±S.E.M.).

Results

Figure 4A:
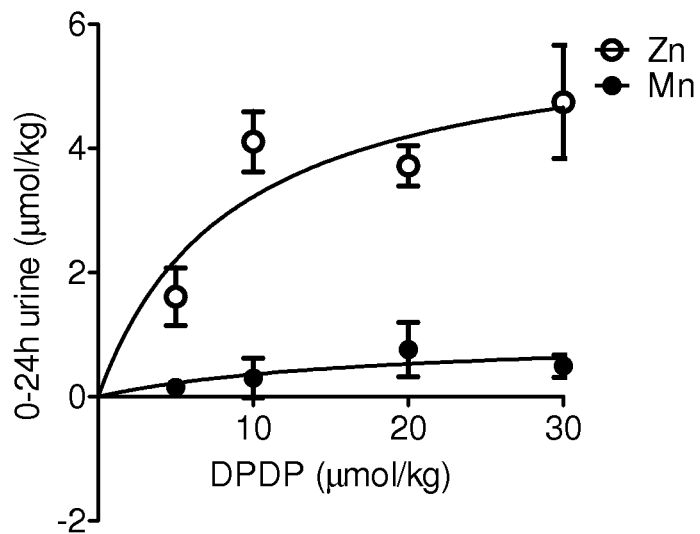
FIGS. 4A and 4B show dose-response curves for 0-24 h Zn and Mn excretion in rats at increasing doses of DPDP (FIG. 4A); mean±S.E.M. (n=10), and the 0-24 h Zn excretion injected with MnDPDP alone or with a combination of MnDPDP and DPDP, expressed as µmol/kg b.w.
Figure 4B:
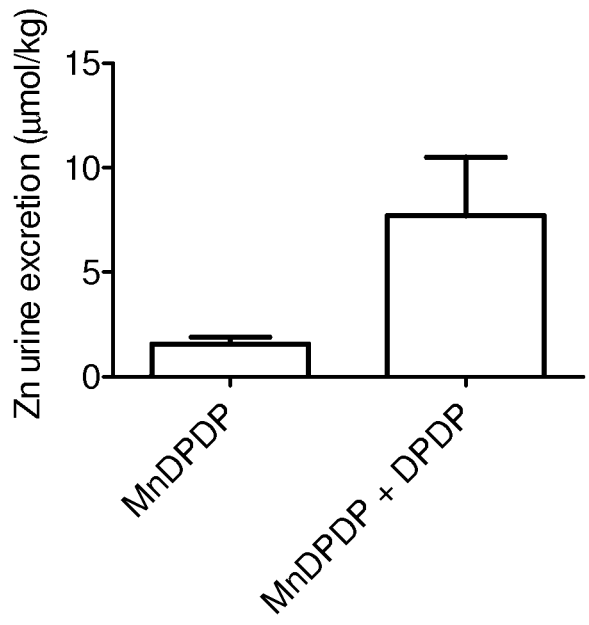

Results are set forth in FIGS. 4A and 4B. The basal 24 h excretion of Zn in two rats receiving 0 µmol/kg b.w. was found to be 0.852 and 0.771 µmol/kg b.w., respectively. The 0-24 h Zn excretion more or less saturated around 4 µmol/kg Zn at a dose of 10 µmol/kg b.w. DPDP (FIG. 4A). Increasing doses of DPDP had just minor effects on the Mn excretion (FIG. 4A). The Zn excretion increased considerably in the 2 rats that received MnDPDP plus DPDP in comparison to the 2 rats that received MnDPDP alone. Taking into consideration the roughly 1000 times higher affinity of Zn for DPDP, compared to Mn, and studies both in rats (Hustvedt et al., Acta Radiol 1997) and humans (Toft et al., 1997), the amount of DPDP needed to saturate Zn excretion is surprisingly low. Furthermore, the relatively small effect of 10 µmol/kg b.w. MnDPDP alone on Zn excretion is also a surprisingly finding. However, as evident from the FIGS. 4A and 4B, DPDP alone or in combination with MnDPDP is capable of increasing Zn excretion considerably, i.e., addition of DPDP, corresponding to about 10 µmol/kg b.w., to MnDPDP stabilizes it from releasing Mn under in vivo conditions.

The fact that only 20% or less of manganese originating from the chelator comes out in the urine after intravenously administration of MnDPDP, at a dose level of 10 µmol/kg b.w., is well known both from studies in humans (Toft et al., 1997) and rats (Hustvedt et al., 1997). It is also known that the chelator, mainly after being dephosphorylated to PLED, is eliminated rapidly and essentially completely from the body via renal excretion (shown by 14C-labelled DPDP in rats and dogs; Hustvedt et al., 1997), with a plasma clearance close to GFR. Furthermore, it is presumed that it is mainly plasma zinc that governs the so-called transmetallation process (Toft et al., 1997), in this case exchange of manganese for zinc. Ideally, one would hence expect that close to 80% of a given dose of MnDPDP (about 8 µmol/kg b.w. based on a dose level of 10 µmol/kg b.w.) should come out in the urine in the form of a zinc-metabolite, mainly as ZnPLED. However, as is shown in Example 4, the amount of zinc in the urine up to 24 hours after administration of 10 µmol/kg b.w. MnDPDP corresponds to only about 2 µmol/kg b.w., i.e., much less than 80% comes out in the urine as zinc-metabolites. A rough recalculation of the human pharmacokinetic data as presented by Toft and coworkers (FIG. 8 in Toft et al., 1997) indicates a somewhat higher but similarly low figure (approximately 3 µmol/kg b.w.) for renal zinc excretion in humans after administration of 10

μmol/kg b.w., i.e., about half of the chelator originating from mother substance MnDPDP has to be excreted through renal excretion in a non-zinc but unknown form. Toft et al. do not discuss the "missing" form, but the fact that relatively less zinc and relatively more manganese is excreted through the kidney when the dose is increased from 5 to 10 μmol/kg b.w. is explained by limited availability of free or loosely bound zinc in the plasma. It should be stressed that transmetallation under in vivo conditions may be a complex process in which several equilibria between zinc and manganese with both low and high molecular weight chelators may be involved (Toft et al., 1997). However, taking in consideration that zinc has a more than 1000 times higher affinity for DPDP or its metabolite PLED and the fact that most of the manganese (more than 80% at a dose of 10 μmol/kg b.w. MnDPDP) dissociates from the chelator, the present findings in Example 4 as shown in FIG. 4B that administration of 10 μmol/kg b.w. DPDP doubles the zinc excretion, in comparison to the same dose of MnDPDP, is an unexpected finding.

In vitro ESR experiments (Schmidt et al., J Biol Inorg Chem 2007; 7:241-248) may suggest that the "missing" form is CaPLED and to a lesser extent MgPLED. Schmidt et al. also reported the stability constant between DPDP and calcium as being around $10^9$, and it may indirectly be concluded from that paper that the corresponding stability constant between magnesium and DPDP is somewhat less. In case the missing form is CaPLED and MgPLED, it could be considered to add surplus of DPDP to the composition, partly or fully, in the form of Ca/MgDPDP. Such an approach may potentially avoid acute depletion of calcium and magnesium upon rapid administration of high doses, which may increase e.g., the cardiovascular safety. It is furthermore difficult to see how added Ca/MgDPDP would have any major negative effect on the stability of MnDPDP, in comparison to DPDP alone. However, whether CaPLED and MgPLED are actually excreted through the kidney after administration of MnDPDP remains to be shown. Another candidate for the missing form could be an iron-bound form, as iron has very high affinity for both DPDP and PLED. However, no effect on hemoglobin after repeat-dose toxicity in either rats, dogs or monkeys has been reported (Larsen & Grant, Acta Radiol 1997; 38:770-779), which indirectly overturns such a candidate.

Example 5

This example tests the therapeutic efficiency of a combination of MnDPDP and DPDP in combination with a cytotoxic drug (paclitaxel).

Method

To test the therapeutic efficacy, initial experiments were conducted in BALB/c female mice (15-20 g), as described by Alexandre et al., JNCI 2006; 98:236-244). Briefly, mice were injected intraperitoneally with vehicle alone (PBS; group 1); with paclitaxel alone (group 2), MnDPDP (Teslascan™) alone or in combination with surplus DPDP, (groups 3-5), as follows:
1. PBS (Control)
2. paclitaxel (20 mg/kg b.w.)
3. paclitaxel (20 mg/kg b.w.)+MnDPDP (1 mg/kg b.w.)
4. paclitaxel (20 mg/kg b.w.)+MnDPDP (1 mg/kg b.w.)+ DPDP (10 μmol/kg b.w.)
5. paclitaxel (20 mg/kg b.w.)+MnDPDP (5 mg/kg b.w.)

Five mice were treated in each group. Paclitaxel was administered on days 0, 2, and 4. On days 0, 2, 4, and 7, mice were administered with MnDPDP±DPDP. Ten days after the first injection the mice were anesthetized and blood samples were withdrawn by heart puncture into EDTA-tubes and blood cell counting (including white blood cell count (WBC); absolute neutrophil (ANC), monocyte and lymphocyte count) was conducted on a CELL-DYN Sapphire analyzer, after the blood samples had been diluted 1:1. Some samples had to be discarded because of clotting but all groups included at least blood from 3 animals.

Results

Figure 5A:
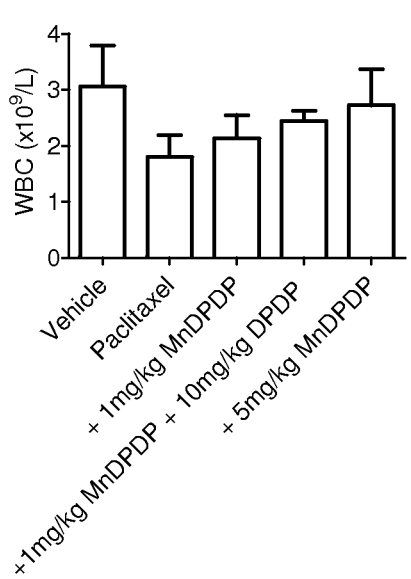
FIGS. 5A-5D show blood cell counts (white blood cell count (WBC), absolute neutrophil count (ANC), monocyte and lymphocyte, respectively) after paclitaxel treatment alone or in combination with MnDPDP±DPDP; mean±S.E.M.; n=3-5 in each group.
Figure 5B:
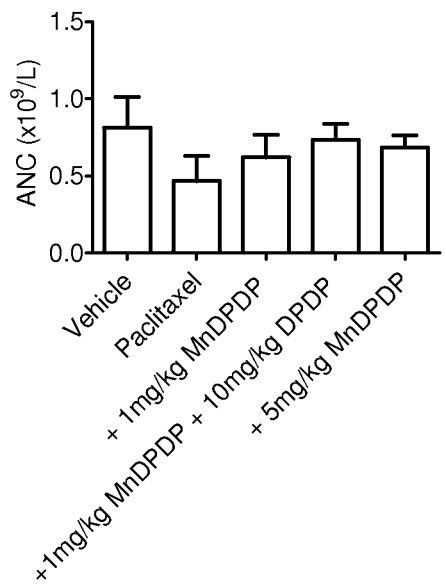
Figure 5C:
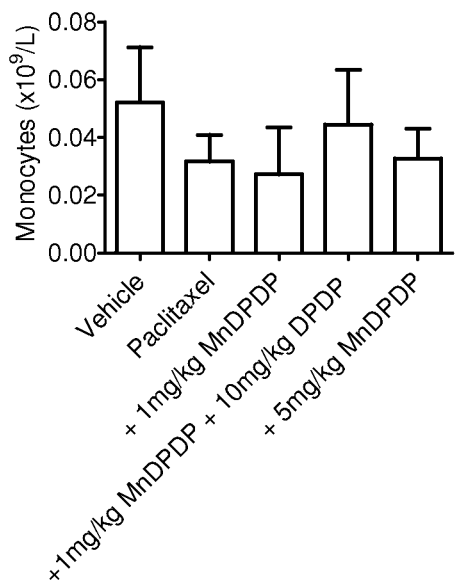
Figure 5D:
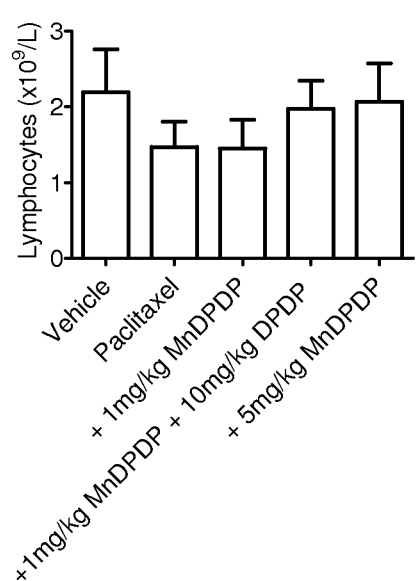

Results are set forth in FIGS. 5A-5D. Paclitaxel reduced the various white blood cells by almost 50% and 1 mg/kg b.w. MnDPDP (corresponding to approximately 1.5 μmol/kg b.w.) in combination with 10 mg/kg b.w. DPDP seems to be as efficacious as to 5 mg/kg b.w. MnDPDP alone to restore the various white blood cells (FIG. 5A). The present results show that surplus of DPDP (in this case approximately 15 μmol/kg b.w.) makes MnDPDP surprisingly efficacious.

Myelosuppression, in particular leucopenia, is a common serious adverse and dose-limiting event during cancer treatment with cytostatic/cytotoxic drugs, including among others paclitaxel. Alexander at al. (2006) has recently shown that 10 mg/kg b.w. MnDPDP (Teslascan™) effectively protect mice against paclitaxel-induced leucopenia. Utilizing the same myelosuppressive mice model as Alexander et al., Example 5 shows that 1 mg/kg b.w. MnDPDP (corresponding to about 1.5 μmol/kg b.w.) in combination with 10 mg/kg b.w. DPDP (corresponding to about 15 μmol/kg b.w.) is as efficacious as 5 mg/kg b.w. MnDPDP alone. Importantly, this improved therapeutic efficacy of MnDPDP is applicable for every indication where MnDPDP or its metabolite MnPLED may show efficacy, e.g., cytostatic/cytotoxic treatments other than paclitaxel, radiation therapy and acute myocardial ischemia-reperfusion injury, among others.

Taken together, the present invention shows how a relatively small amount of added DPDP makes MnDPDP therapeutically much more efficacious and less neurotoxic. The amount of needed DPDP (corresponding to a dose about 10 μmol/kg b.w.) correlates more to the documented imaging dose of 5 to 10 μmol/kg b.w. MnDPDP. The improved composition, regarding increased therapeutic efficacy and decreased neurotoxicity, may hence be looked upon as a metal-chelator complex containing deficits of the metal.

From Example 1 it may be concluded that the addition of DPDP doubles the in vivo stability of MnDPDP/MnPLED at a dose level of 10 μmol/kg b.w. However, the present examples and the above discussion around zinc-driven transmetallation of MnDPDP/MnPLED suggest that the in vivo instability of MnDPDP is reciprocally correlated to the dose of MnDPDP, i.e., relatively more manganese will be exchanged for zinc at lower dose levels. It is therefore concluded that added surplus of DPDP renders MnDPDP much more efficacious than Example 1 suggests. As has been stated elsewhere, MnDPDP probably has to be metabolized into MnPLED before it can exert cytoprotective effects. Previous data (e.g., Karlsson et al., 2001, EP 0910360, U.S. Pat. No. 6,147,094) have demonstrated MnPLED to be much more efficacious than MnDPDP, even after metabolic correction has been taken in consideration, anticipating that about ⅓ of MnDPDP is metabolized into MnPLED, as suggested by Toft et al., 1997. This anticipation is done from pharmacokinetic data at a dose level of 10 μmol/kg b.w. MnDPDP. On the other hand, at a lower dose level, enough zinc will probably be available for exchanging manganese more or less completely, resulting in very little or no MnPLED. This may in turn explain why added surplus of DPDP increases therapeutic efficacy of MnDPDP much more than Example 1 suggests.

The examples and specific embodiments set forth herein are illustrative in nature only and are not to be taken as limiting the scope of the invention defined by the following claims Additional specific embodiments and advantages of the present invention will be apparent from the present disclosure and are within the scope of the claimed invention.

What is claimed is:

1. A method of reducing uptake of manganese to the brain of a patient when a pathological condition in a patient caused by superoxide radicals is treated by administration of manganese N,N'-bis-(pyridoxal-5-phosphate)-ethylenediamine-N,N'-diacetic acid (MnDPDP) or a salt thereof in an amount effective to treat the pathological condition, the method comprising administering, as a second component, N,N'-bis-(pyridoxal-5-phosphate)-ethylenediamine-N,N'-diacetic acid (DPDP) or a salt or non-manganese complex thereof in an amount effective to reduce uptake of manganese to the brain of the patient as compared with administration of MnDPDP in the absence of the second component, wherein the second component is administered in an amount of about 1 to 20 μmol/kg body weight, wherein MnDPDP and the second component are included in a MnDPDP:second component molar ratio in the range of about 1:1 to 1:10, and wherein the administration of MnDPDP and/or the administration of the second component are optionally together with one or more physiologically acceptable carriers and/or excipients.

2. A method according to claim 1, wherein the second component is DPDP, calcium DPDP or magnesium DPDP, or a combination of two or more thereof.

3. A method of reducing uptake of manganese to the brain of a patient when a pathological condition in a patient caused by superoxide radicals is treated by administration of a manganese complex of a compound of Formula I in an amount effective to treat the pathological condition, the method comprising administering, as a second component, a compound of Formula I or a non-manganese metal complex of a compound of Formula I in an amount effective to reduce uptake of manganese to the brain of the patient as compared with administration of the manganese complex in the absence of the second component, wherein the second component is administered in an amount of about 1 to 20 μmol/kg body weight, wherein the manganese complex and the second component are included in a manganese complex:second component molar ratio in the range of about 1:1 to 1:10, and wherein the administration of the manganese complex and/or the administration of the second component are optionally together with one or more physiologically acceptable carriers and/or excipients,

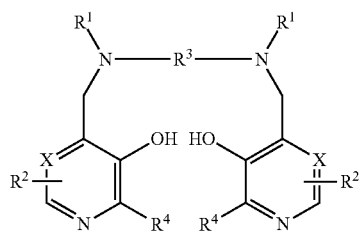

Formula I wherein
X represents CH,
each $R^1$ represents $CH_2COR^5$;
$R^5$ represents hydroxy;

each $R^2$ independently represents $ZYR^6$ wherein Z represents a bond, $CH_2$ or $—CH_2O—$;
Y represents a bond or an oxygen atom;
$R^6$ is a hydrogen atom, $COOR^8$, alkyl, alkenyl, cycloalkyl, aryl or aralkyl group optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;
$R^7$ is hydroxy, optionally hydroxylated, optionally alkoxylated alkyl or aminoalkyl group;
$R^8$ is a hydrogen atom or an optionally hydroxylated, optionally alkoxylated alkyl group;
provided that each $ZYR^6$ includes a $—CH_2O—$ linkage to the respective pyridine ring;
M is a hydrogen atom or one equivalent of a physiologically tolerable cation;
$R^3$ represents ethylene; and
each $R^4$ independently represents hydrogen or $C_{1-3}$ alkyl.

4. A method according to claim 3, wherein $R^6$ is a mono- or poly(hydroxy or alkoxylated) alkyl group, $OR^8$ or $OP(O)(OR^8)R^7$; $R^7$ is hydroxy, or an unsubstituted alkyl or aminoalkyl group; and $R^8$ is hydrogen.

5. A method according to claim 3, wherein the manganese complex has a $K_a$ value in the range of from $10^8$ to $10^{24}$.

6. A method according to claim 3, wherein the second component has a lower $K_a$ value for $Mn^{2+}$ than the corresponding $K_a$ value for zinc ($Zn^{2+}$), by a factor of at least 10.

7. A method according to claim 3, wherein the manganese complex and the second component are included in a manganese complex:second component molar ratio in the range of about 1:2 to 3:4.

8. A method according to claim 3, wherein said condition is a cytotoxic or cytostatic drug injury.

9. A method according to claim 8, wherein the cytotoxic or cytostatic drug is a cancer treatment drug.

10. A method according to claim 8, wherein the cytotoxic or cytostatic drug comprises at least one of doxorubicin, oxaliplatin, 5-fluorouracil or paclitaxel.

11. A method according to claim 3, wherein said condition is an ischemia-reperfusion-induced injury.

12. A method according to claim 3, wherein said condition is a result of myocardial ischemia-reperfusion-induced injury.

13. A method according to claim 3, wherein said condition is associated with a thrombolytic treatment, a cardiopulmonary bypass, or percutaneous transluminal angioplasty, or is a result of cardiac or organ transplantation surgery.

14. A method according to claim 3, wherein said condition is acetaminophen-induced acute liver failure.

15. A method according to claim 3, wherein said condition is a pathological condition of iron.

16. A method according to claim 3, wherein said condition is thalassemia, sickle cell anemia, or transfusional hemosiderosis.

17. A method according to claim 3, wherein said condition is hepatitis-induced liver cirrhosis.

18. A method according to claim 3, wherein said condition is a radiation-induced injury.

19. A method according to claim 3, wherein the manganese complex and the second component are administered simultaneously.

20. A method according to claim 3, wherein the manganese complex and the second component are administered sequentially.

21. A method according to claim 3, wherein the manganese complex and the second component are included in a manganese complex:second component molar ratio in the range of about 1:1 to 1:5.

22. A method according to claim 3, wherein the manganese complex and the second component are included in a manganese complex:second component molar ratio of about 1:5.

23. A method according to claim 3, wherein the second component is administered in a greater molar amount relative to the manganese complex.

24. A method according to claim 1, wherein said condition is a cytotoxic or cytostatic drug injury.

25. A method according to claim 24, wherein the cytotoxic or cytostatic drug is a cancer treatment drug.

26. A method according to claim 24, wherein the cytotoxic or cytostatic drug comprises at least one of doxorubicin, oxaliplatin, 5-fluorouracil or paclitaxel.

27. A method according to claim 1, wherein said condition is an ischemia-reperfusion-induced injury.

28. A method according to claim 1, wherein said condition is a result of myocardial ischemia-reperfusion-induced injury.

29. A method according to claim 1, wherein said condition is associated with a thrombolytic treatment, a cardiopulmonary bypass, or percutaneous transluminal angioplasty, or is a result of cardiac or organ transplantation surgery.

30. A method according to claim 1, wherein said condition is acetaminophen-induced acute liver failure.

31. A method according to claim 1, wherein said condition is a pathological condition of iron.

32. A method according to claim 1, wherein said condition is thalassemia, sickle cell anemia, or transfusional hemosiderosis.

33. A method according to claim 1, wherein said condition is hepatitis-induced liver cirrhosis.

34. A method according to claim 1, wherein said condition is a radiation-induced injury.

35. A method according to claim 1, wherein the MnDPDP and the second component are administered simultaneously.

36. A method according to claim 1, wherein the MnDPDP and the second component are administered sequentially.

37. A method according to claim 1, wherein the MnDPDP and the second component are included in a first component: second component molar ratio in the range of about 1:1 to 1:5.

38. A method according to claim 1, wherein the DPDP is administered in a greater molar amount relative to the first component.

39. A method according to claim 3, wherein $R^6$ is a hydrogen atom.

40. A method of reducing uptake of manganese to the brain of a patient when a pathological condition in a patient caused by superoxide radicals is treated by administration of a manganese complex of a compound of Formula I in an amount effective to treat the pathological condition, wherein the pathological condition is: a cytotoxic or cytostatic drug injury; an ischemia-reperfusion-induced injury; a result of myocardial ischemia-reperfusion-induced injury; associated with a thrombolytic treatment, a cardiopulmonary bypass, or percutaneous transluminal angioplasty; a result of cardiac or organ transplantation surgery; acetaminophen-induced acute liver failure; a pathological condition of iron; thalassemia; sickle cell anemia; transfusional hemosiderosis; hepatitis-induced liver cirrhosis; or radiation-induced injury, the method comprising administering, as a second component, a compound of Formula I or a non-manganese metal complex of a compound of Formula I in an amount effective to reduce uptake of manganese to the brain of the patient as compared with administration of the manganese complex in the absence of the second component, wherein the second component is administered in an amount of about 1 to 20 μmol/kg body weight, wherein the manganese complex and the second component are included in a manganese complex: second component molar ratio in the range of about 1:1 to 1:10, and wherein the administration of the manganese complex and/or the administration of the second component are optionally together with one or more physiologically acceptable carriers and/or excipients,

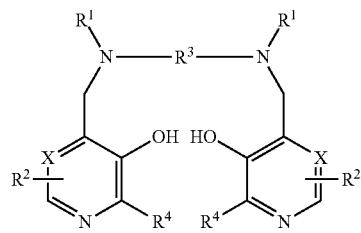

Formula I wherein
X represents CH,
each $R^1$ represents $CH_2COR^5$;
$R^5$ represents hydroxy;
each $R^2$ independently represents $ZYR^6$ wherein Z represents a bond, $CH_2$ or $—CH_2O—$;
Y represents a bond or an oxygen atom;
$R^6$ is a hydrogen atom, $COOR^8$, alkyl, alkenyl, cycloalkyl, aryl or aralkyl group optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;
$R^7$ is hydroxy, optionally hydroxylated, optionally alkoxylated alkyl or aminoalkyl group;
$R^8$ is a hydrogen atom or an optionally hydroxylated, optionally alkoxylated alkyl group;
provided that each $ZYR^6$ includes a $—CH_2O—$ linkage to the respective pyridine ring;
M is a hydrogen atom or one equivalent of a physiologically tolerable cation;
$R^3$ represents ethylene; and
each $R^4$ independently represents hydrogen or $C_{1-3}$ alkyl.

41. A method according to claim 40, wherein the second component is DPDP, calcium DPDP or magnesium DPDP, or a combination of two or more thereof.

* * * * *